United States Patent [19]

Kelly et al.

[11] 4,396,385
[45] Aug. 2, 1983

[54] FLOW METERING APPARATUS FOR A FLUID INFUSION SYSTEM

[75] Inventors: Timothy G. Kelly, Silver Spring; David A. Lohr, Ellicott City; Peter A. St. John, Adelphi, all of Md.

[73] Assignee: Baxter Travenol Laboratories, Inc., Deerfield, Ill.

[21] Appl. No.: 213,353

[22] Filed: Dec. 5, 1980

[51] Int. Cl.³ .............................................. A61M 5/20
[52] U.S. Cl. ............................ 604/152; 128/DIG. 12; 417/22
[58] Field of Search ............. 128/214 E, 214 F, 214.2, 128/273, DIG. 12; 417/22

[56] References Cited
U.S. PATENT DOCUMENTS

3,985,133 10/1976 Jenkins et al. .................. 128/214 F
4,131,393 12/1978 Magnussen ............................ 417/22
4,137,913 2/1979 Georgi ............................ 128/214 F

Primary Examiner—Dalton L. Truluck
Attorney, Agent, or Firm—Paul C. Flattery; John P. Kirby, Jr.; Eugene Cummings

[57] ABSTRACT

Metering apparatus for controlling the flow of fluid through a fluid infusion system at an operator-designated rate includes a single-use cassette having a syringe-type pump in the flow system. The cassette is removably mounted on actuator apparatus which drives the syringe plunger through alternate fill and pump modes to advance fluid through the system. To provide compensation for the lack of flow in the system during fill strokes, the plunger is advanced at a higher compensation rate for first and second portions of the pump stroke immediately preceding and immediately following each fill stroke, with the pump stroke advancing at the designated rate therebetween. This results in an average flow rate which corresponds to the designated rate. By making the first and second compensations of equal duration, the effect of the fill cycles on the regularity of the average flow rate is minimized.

34 Claims, 9 Drawing Figures

FLOW METERING APPARATUS FOR A FLUID INFUSION SYSTEM

BACKGROUND OF THE INVENTION

The present invention relates generally to fluid infusion systems, and more particularly to an improved flow metering apparatus for such systems.

The infusion of fluids into the human body is usually accomplished by means of an administration set and metering apparatus which controls the rate of flow of fluid through the set. Cassette-type metering apparatus, wherein a disposable cassette pumping element is integrally included in the administration set, and actuated by external apparatus when in use, has proven particularly attractive for this purpose because it is capable of providing a very precise control of fluid flow through the system, but does not introduce the possibility of leakage or contamination.

One form of cassette in wide use in fluid infusion systems utilizes a syringe-type pumping element in conjunction with a two-position valve which connects the metering chamber of the syringe to either the fluid source or the needle adaptor of the system. In use, the valve connects the metering chamber to the source while the plunger of the syringe is being retracted (fill stroke), and to the needle adaptor while the plunger is being advanced (pump stroke), thereby advancing fluid through the system Typically, the actuator means for the cassette includes an actuator member which engages the plunger rod of the syringe to reciprocatively drive the plunger. Preferably, a stepping motor is used to drive the actuator member for optimum metering accuracy. Additional actuator means in the actuator apparatus engage the two position valve of the cassette so that fluid is directed into the syringe housing during the fill stroke, and toward the needle adaptor of the administration set during the pump stroke.

In many applications, such as where medication is being administered intravenously, it is necesssary that the actuation of the cassette pumping element be precisely controlled to infuse a predetermined volume of fluid at a predetermined rate. This requirement for precision control and actuation is complicated by the nature of the syringe pumping element, which because of its comparatively small volume must be filled and emptied repeatedly during the infusion process. Since pumping is not taking place while the metering chamber is being filled, to maintain metering accuracy it is necessary to compensate the delivery rate of each pump stroke for time lost in the accompanying fill stroke. This may be accomplished by increasing the delivery rate to a predetermined greater rate for a predetermined portion of the pump stroke so that the average flow rate at the end of each fill-pump cycle is the desired infusion rate.

The present invention provides an improved apparatus and method for syringe-type cassette pumps wherein compensation for the fill stroke is provided by compensating periods of increased pumping rate at both the beginning and end of each pump stroke. This provides a more uniform average pumping rate throughout the fill-pump cycle, since the higher infusion rate occurs before and after the interruption of the pump stroke by the fill stroke.

Accordingly, it is a general object of the present invention to provide a new and improved system for infusing fluids into the human body.

It is a more specific object of the present invention to provide a new and improved metering apparatus for infusing fluids into the human body.

It is another object of the present invention to provide new and improved cassette-type metering apparatus which provides a more uniform flow rate.

It is another object of the present invention to provide new and improved cassette-type metering apparatus for infusing fluids into the human body wherein compensation during the pump stroke is provided immediately preceeding and immediately following the fill stroke for improved flow continuity.

It is another object of the present invention to provide a new and improved method for infusing fluids into the human body.

It is another object of the present invention to provide a new and improved method for infusing fluids into the human body which provides a more uniform average flow rate.

SUMMARY OF THE INVENTION

The invention is directed to metering apparatus for use in conjunction with a fluid system for infusing fluids at an operator-selected rate into the human body. The apparatus comprises syringe pump means in the flow system, including a plunger having alternate fill and pump strokes, for establishing fluid flow through the system. Actuator means reciprocatively drive the plunger so as to provide fill strokes of relatively short duration and pump strokes of relatively longer duration at the operator-selected flow rate, the average flow through the flow system as a result thereof being less than the operator-selected rate as a result of the intervening fill strokes between the pump strokes. Flow compensation means increase the rate of each pump stroke to a relatively higher compensation rate for a first predetermined compensation period immediately following the preceding fill stroke, and for a second predetermined compensation period immediately preceding the following fill stroke, the intervening portion of each pump stroke being at the operator selected rate, whereby the resulting average flow rate through the flow system comprises the operator-selected rate.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

DESCRIPTION OF THE PREFERRED EMBODIMENT

Figures 1, 2:
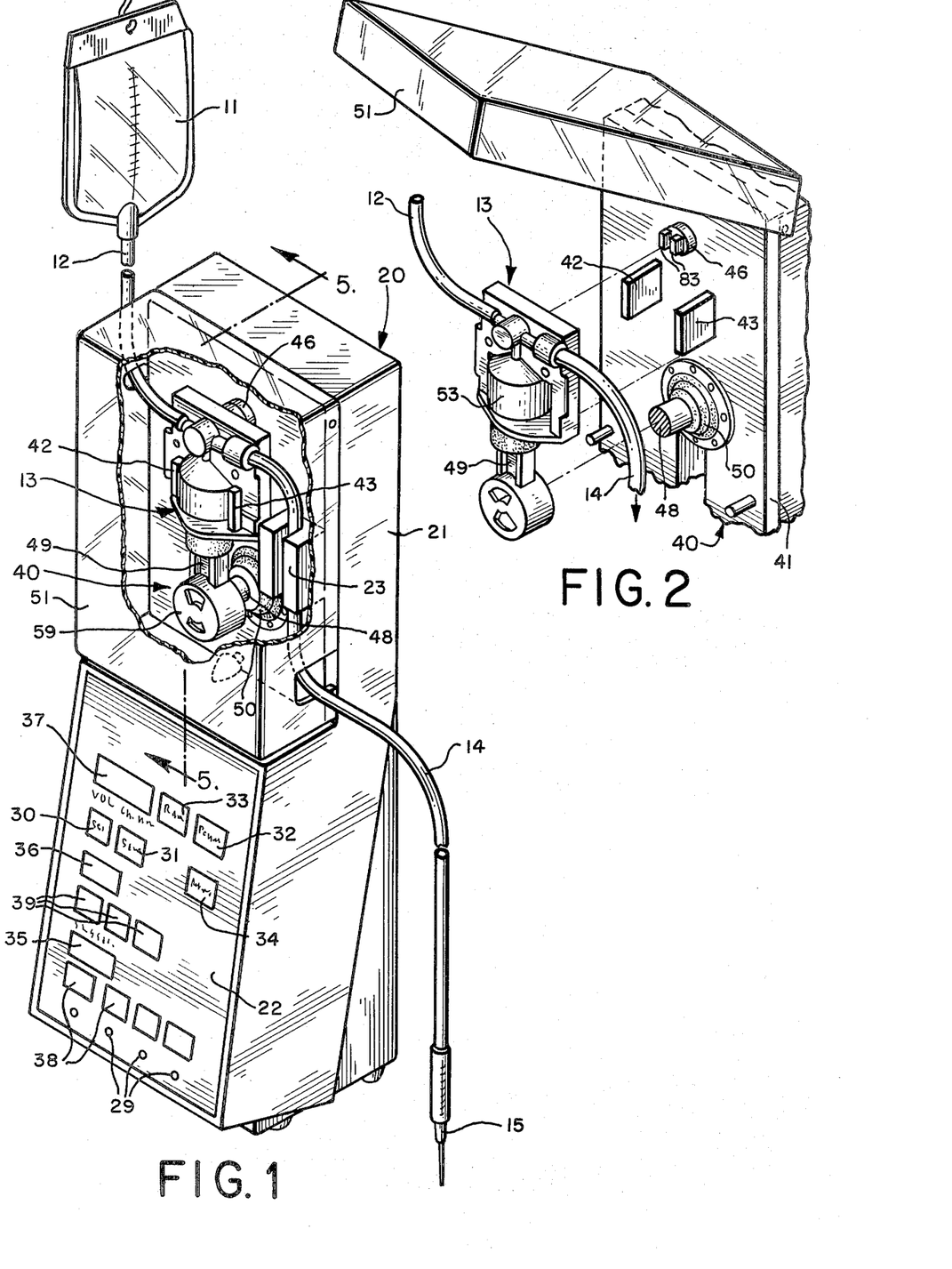
FIG. 1 is a perspective view of an infusion system and flow metering apparatus constructed in accordance with the invention.
FIG. 2 is a perspective view of the cassette actuator station of the flow metering apparatus of FIG. 1.

Referring to the Figures, and particularly to FIG. 1, an infusion system constructed in accordance with the invention for injecting a fluid into a vein or artery from a reservoir 11 may include a disposable administration set consisting of a first tubing segment 12, a pump cassette 13, a second tubing segment 14, and a needle adaptor 15 to which a needle of appropriate size and shape may be fitted. The administration set, which may be conventional in design and construction, is preferably packaged in a sterile and nonpyrogenic condition for a single one-time use.

The pump cassette 13 of the administration set is received within a pump actuator apparatus 20, which includes necessary mechanical actuating means for the cassette, as well as electronic control means for controlling the operation of the actuating means. As seen in FIG. 1, the actuator apparatus 20 includes a housing 21 having an inclined front surface on which a control panel 22 is contained. This control panel allows the operator to control and monitor the operation of the cassette actuator apparatus.

The operating mode of the actuator apparatus is controlled by means of a push-button START switch 30, a push-button STOP switch 31, and an ON-OFF power switch 32. An additional RESET push-button switch 33 is provided for clearing previously accumulated volumes and a PURGE switch 34 is provided for obtaining rapid continuous operation of the actuator apparatus as when purging air from the fluid infusion system. Each of these push button switches may include an internal indicator lamp which provides a positive indication of the operating mode of the apparatus.

Control panel 22 further includes a digital display 35 of volume to be infused, a digital display 36 of selected fluid flow rate, and a digital display 37 of volume actually infused. The volume to be infused is preset by the operator by means of a set of push button switches 38, and the infusion rate is preset by means of a second set of push button switches 39. Various warning functions such as the detection of a fluid absence in the system or the occurrence of a low battery condition, are indicated by a plurality of warning lights 29 at the bottom of the panel.

To provide an aesthetically pleasing front panel surface free of openings which might harbor contaminants, front panel 22 is preferably constructed from a single seamless panel having transparent sections for viewing readouts 35-37. The push button switches 30-34, 38 and 39 associated with these displays are preferably pressure-sensitive switches, which respond to very small deformations of the front panel brought about by finger pressure from the operator to actuate their respective circuits.

Referring to FIG. 2, in use cassette 13 is received within an actuator station 40 comprising a generally flat and vertical front plate above panel 22. A pair of flat horizontally-spaced mounting tabs 42 and 43 project from the front plate and are received in complementarily dimensional slot-shaped recesses 44 and 45 (FIGS. 3 and 4) in the cassette to secure the cassette in position. Actuation of the cassette is accomplished by a rotary valve actuator member 46 which projects through mounting plate 41 to operatively engage a rotary valve member 47 within the cassette, and a syringe actuator member 48 which projects through the mounting plate below the valve actuator member to engage the actuator stem 49 of the cassette syringe. A flexible boot 50 formed of rubber or other flexible material is provided around syringe actuator member 48 to form a seal which allows movement of the actuator without allowing fluids to reach the interior of the pump apparatus.

An added degree of protection for the cassette when in use is provided by a cover 51 which is pivotally mounted at its top end to housing 21 so as to cover the cassette and cassette actuator station when closed. This cover is preferably formed of a transparent material to allow the operation of the cassette to be visually monitored while the pump is in use.

Figures 5, 6:
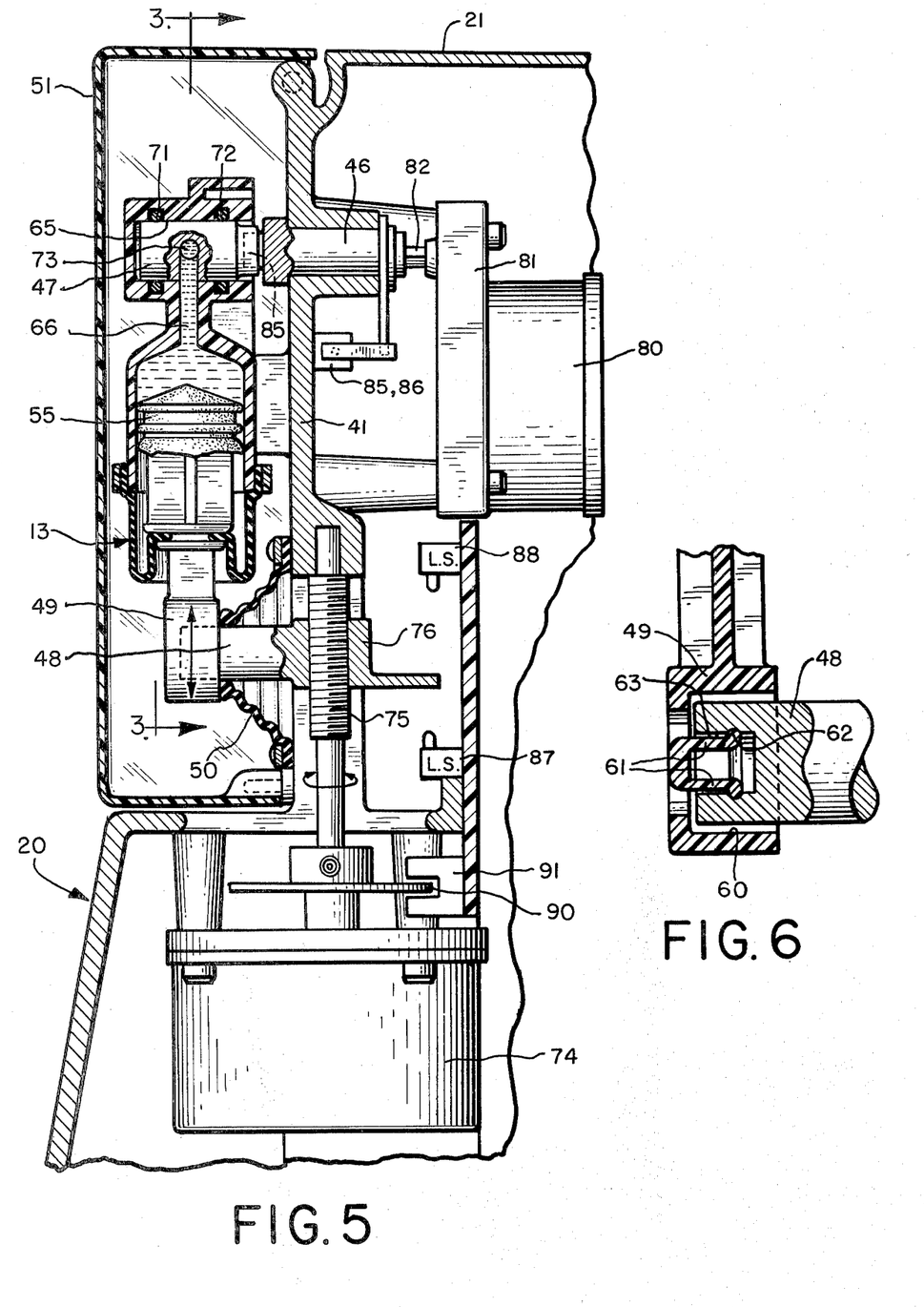
FIG. 5 is an enlarged cross-sectional view of the cassette and cassette actuator station showing the cassette in an operating position.
FIG. 6 is an enlarged cross-sectional view of the syringe actuator member of the cassette actuator station and plunger rod of the cassette taken along line 6—6 of FIG. 5.

Referring to FIGS. 5 and 6, cassette 13 is seen to include a generally rectangular body portion 52 within which are defined the elongated slots 44 and 45 within which mounting tabs 42 and 43 are received, respectively. A syringe portion 53 generally within the frame portion 52 includes a generally cylindrical metering chamber 54 within which a plunger 55 is slidably disposed. An annular ridge 56 establishes a sliding liquid-seal engagement between the plunger and the walls of the metering chamber. The plunger includes actuator stem 49 which extends from the body portion, terminating in a snap-on engaging portion 59 of increased diameter. As seen in FIGS. 5 and 6, the engaging portion 59 preferably includes a recessed portion 60 within which a pair of projecting resilient latch members 61 project. When the cassette is installed in the actuator station, these latch members 61 engage an annular recess 62 on the inside wall of an axial bore 63 in actuator member 48. As a result of this engagement, the plunger actuator 49 is securely engaged to actuator member 48 and can be removed only with a deliberate outward pull by the operator.

To provide for filling and emptying of metering chamber 54, cassette 13 includes a bore shaped chamber 65 within which the rotatable valve member 47 is seated. Fluid communication is established between this valve member and metering chamber 54 by means of a passageway 66 which extends between the valve member and the end of chamber 54. When the valve member 65 is rotated to the fill position shown in FIG. 3, conduit 66 is connected to an inlet conduit 67 and fluid is drawn into the chamber through tubing segment 12. When valve member 65 is rotated to the pump position shown in FIG. 4, conduit 66 is connected to an outlet conduit 68 and fluid is discharged from chamber 54 through tubing segment 14.

A pair of O-ring liquid seal members 71 and 72 may be provided in respective annular recesses at either end of the valve member to prevent leakage of fluid within the valve. In accordance with conventional practice, the rotary valve member includes an angled passageway 73 which establishes fluid communication between conduits 66 and 67, or between conduits 66 and 68, as required.

Mechanical actuation of plunger 55 is accomplished by means of a stepper motor 74 within housing 21. The output shaft of the stepper motor includes a lead screw 75 arranged behind panel 41 generally parallel to the direction of movement of the plunger. Upon rotation of the lead screw, a follower 76 threadedly engaged to the lead screw is caused to move axially along the lead screw, the direction and extent of travel depending on the direction and extent of rotation of the stepping motor output shaft. Plunger actuator member 48 is carried along with follower 76, so that upon movement of the follower syringe plunger 55 is moved within chamber 54. Consequently, by selective actuation of motor 74 in alternately clockwise and counterclockwise directions, plunger 55 is reciprocatively driven within metering chamber 54 to alternately fill and empty the cassette syringe to pump fluid through the system.

To provide for positioning of valve member 47 in accordance with the operating mode of plunger 55, actuator apparatus 20 inlcudes valve positioning means in the form of a motor 80. This motor is coupled through a reduction gear assembly 81 of conventional design and construction to a drive shaft 82. This drive shaft is in turn coupled to the valve actuator member 46, which is journaled in panel 41 so as to include a projecting portion extending from the front of the panel for engaging the valve member 47 of the cassette. A pair of axially projecting pins 83 on member 46 engage complementarily dimensioned recesses 84 (FIG. 5) on the valve members 47 to insure rotational coupling of the two members.

As a result of the rotational coupling between motor 80 and valve member 47, the valve can be quickly shifted between fill and pump positions. To prevent operation of the plunger when the valve has not been properly positioned, valve position monitoring means in the form of electrical switches 85 and 86 are provided within housing 21 in operative engagement with actuator member 46. When member 46 is in the fill position, switch 85 is closed. When member 46 is in the pump position, switch 86 is closed. As will be seen presently, these switches provide inputs to the pump control system useful in preventing premature operation of plunger 55.

To monitor the position of the plunger, pump apparatus 20 inlcudes limit switches 87 and 88 which are actuated upon follower member 76 reaching lower and upper positions, corresponding to plunger open and plunger closed operating limits, respectively. The rotation of stepper motor 74 is monitored by means of a disc 90 and a photoelectric disc rotation sensor 91. Rotation of the output shaft of stepper motor 74 in response to applied stepping pulses results in the generation of output pulses from rotation monitor 91. By comparing these output pulses with applied stepper pulses, a stall warning system within the control circuitry of the pump apparatus is able to warn of a stalled condition.

Figure 7:
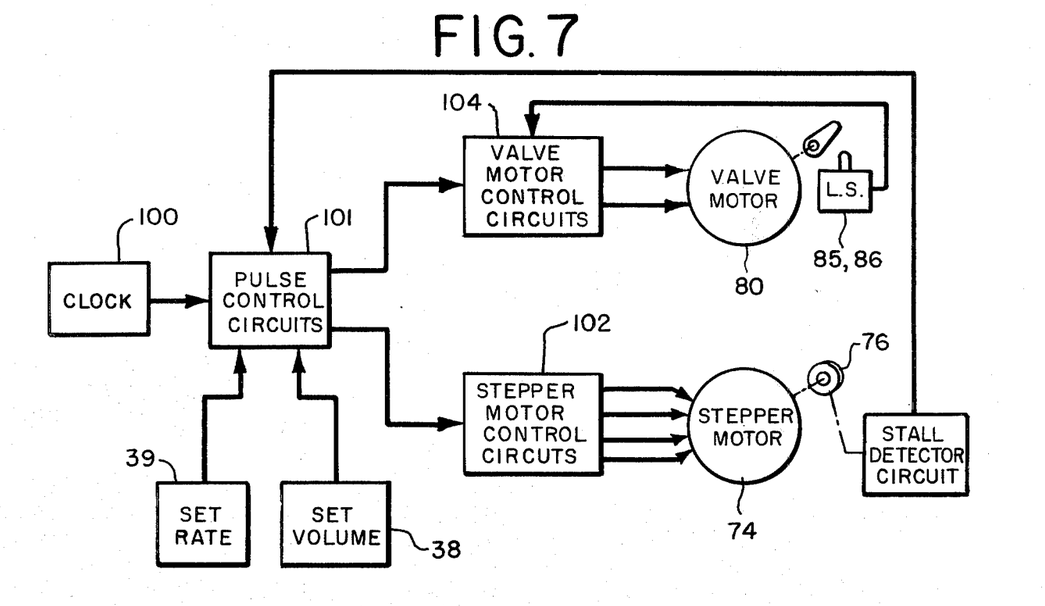
FIG. 7 is a simplified functional block diagram of the basic elements of the pump control system.

The control system provided in the cassette actuator apparatus 20 is shown in basic form in the simplified block diagram of FIG. 7. The system includes a constant frequency oscillator or clock 100 which provides a source of pulses at a fixed rate for operation of the various circuits of the system. These pulses are applied to pulse rate control circuits 101 wherein the rate and volume set by the user are taken into account in generating motor control pulses having a repetition rate appropriate for achieving a desired average flow rate through the infusion system. These motor control pulses are applied to stepper motor control circuits 102 of conventional design, which generate appropriate multi-phase motor stepping signals for application to the windings of the stepper motor.

The operation of the stepper motor is monitored by a motion sensor circuit 103, which responds to the output of rotation sensor 91 to provide an inhibit signal to pulse control circuits 101 in the event the stepper motor becomes stalled. Similarly, the position of follower 76 on lead screw 75 is monitored by limit switch 87, which provides a signal to pulse control circuits 101 upon the follower reaching its full open position. As will be seen presently, this signal can be utilized in initiating subsequent fill-pump cycles.

The operation of the valve control motor 80 is controlled by valve motor control circuits 104 which respond to control signals developed by pulse control circuits 104 to reposition the flow control valve upon completion of the fill and pump strokes of the cassette syringe. Limit switches 85 and 86 provide outputs to motor control circuits 104 indicative of the position of valve 47. In the event that valve 47 is not properly positioned, an output signal is produced by control circuits 104 to inhibit further operation of pulse control circuits 101.

Figure 3:
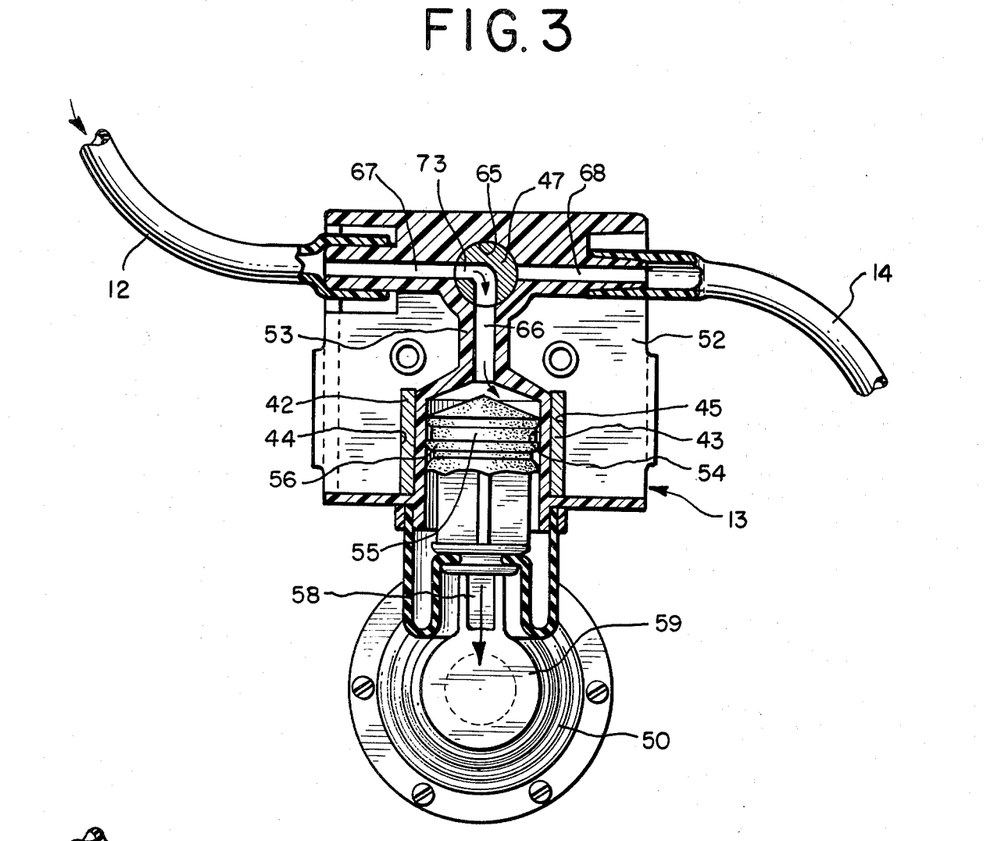
FIG. 3 is an enlarged front elevational view of the cassette in position on the actuator station of the pump apparatus showing the operation of the pump during a fill stroke.
Figure 4:
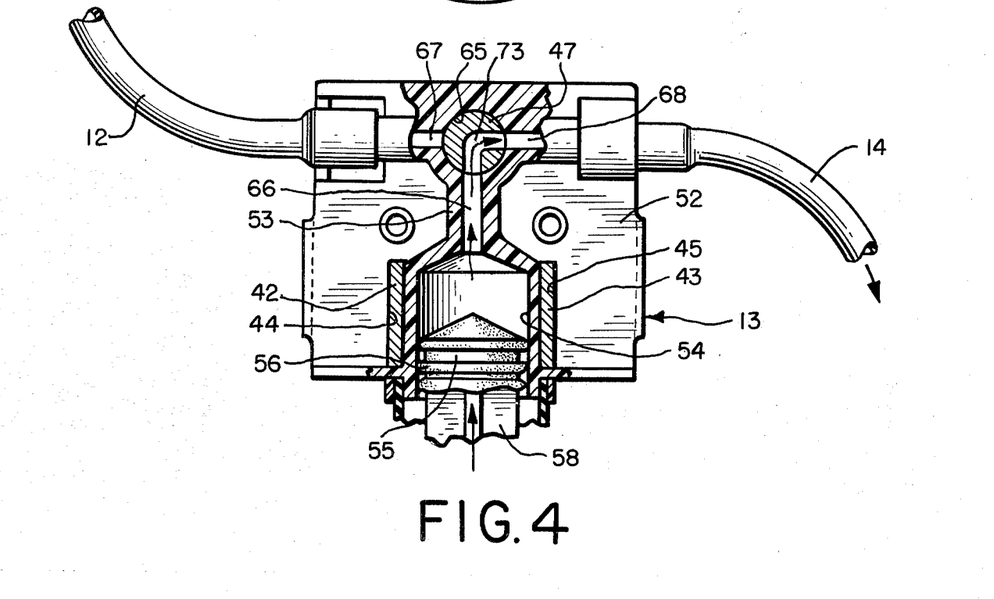
FIG. 4 is an enlarged front elevational view similar to FIG. 3 showing the operation of the pump during a pump stroke.

In operation, valve 47 is positioned to the fill position shown in FIG. 3 and plunger 55 is retracted to cause chamber 54 to be filled with fluid. Then, after the plunger has been fully retracted, valve 47 is positioned to the pump position shown in FIG. 4, and plunger 55 is driven forward to move fluid from the chamber. After the plunger has reached its full moved position, extended valve 47 is again moved to its fill position, and the cycle begins anew. Thus, with each fill-pump cycle a predetermined quantity of fluid equal to the volume of metering chamber 54 is dispensed from the cassette. The rate at which this quantity is dispensed is dependent on the speed at which plunger 55 is moved during the pump stroke. This rate of movement is accurately controlled by varying the frequency of the stepping pulses applied to stepper motor 74; the higher the frequency, the greater the rotational speed of the motor and the higher the flow rate.

Although the fill stroke is typically accomplished at a relatively high rate compared to the pump stroke, it nevertheless remains that an error is introduced in the average rate realized because fluid is not pumped by the cassette during fill strokes. Consequently, to obtain a desired average flow rate within the flow system it is necessary to compensate the pump stroke for time lost during the fill stroke. In accordance with the invention, this is accomplished by providing at the beginning and end of each pump stroke a compensating period during which the plunger 55 is operated at an increased rate to compensate for time lost during the succeeding fill stroke. Providing compensation in this manner minimizes overall fluctuation in flow, since the higher flow rates immediately precede and follow the period of no flow, i.e., the fill stroke. This minimizes the effect of flow interruption during the fill stroke for more even flow.

Figure 8:
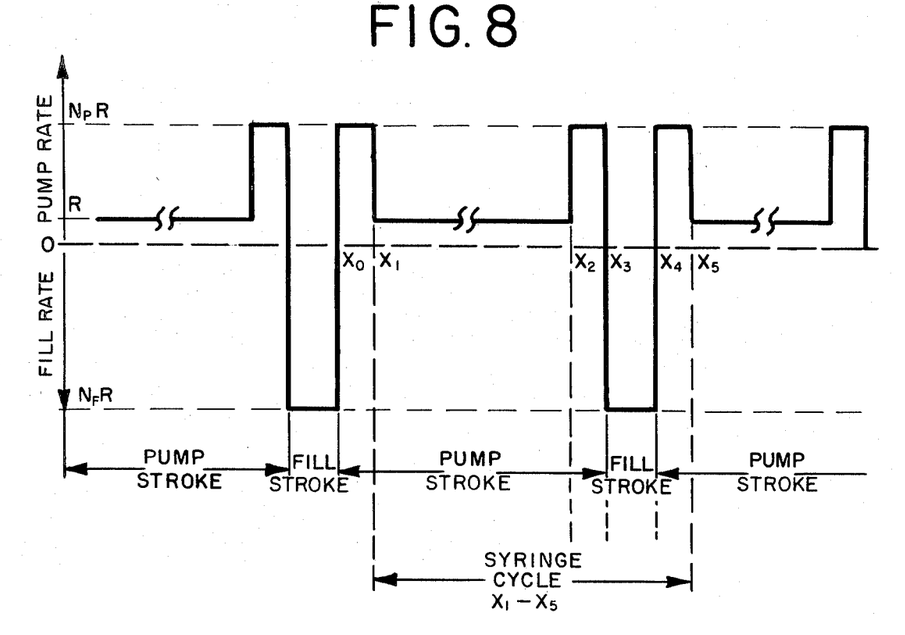
FIG. 8 is a graphical depiction of the mode of operation of the pump.

The method by which the pump apparatus of the invention compensates for pumping time lost during refill periods is illustrated by the plot of plunger rate versus plunger position shown in FIG. 8. There it is seen that during each pump stroke $X_0$-$X_3$ the plunger rate is momentarily increased from a nominal rate R to an increased rate NpR, where Np is a selected constant greater than one, such as four in the present embodiment, and R is an operator-selected infusion rate, for a first period $X_0$-$X_1$ at the beginning of the pump stroke, and for a second period $X_2$-$X_3$ at the end of the pump stroke. Between the two compensation periods, for a period of $X_1$-$X_2$, the plunger operates at the operator-selected rate. The length of the compensation periods $X_0$-$X_1$, and $X_2$-$X_3$ is selected so that the overall average flow rate, R avg, taking into account the refill time of the plunger, corresponds to the rate R selected by the operator.

This method of operation is facilitated by the use of stepper motor 74 for driving the plunger of cassette 13. Since each pulse applied to the stepper motor results in an incremental rotation of the stepper motor output shaft, and hence an incremental advance of the plunger, a specific predictable quantity of fluid is dispensed with each applied stepping pulse. Thus, by generating stepping pulses at various predetermined time intervals, the control system of the apparatus achieves the method of operation illustrated in FIG. 8. One practical control system for providing such pulses is shown in the functional block diagram of FIG. 9.

Figure 9:
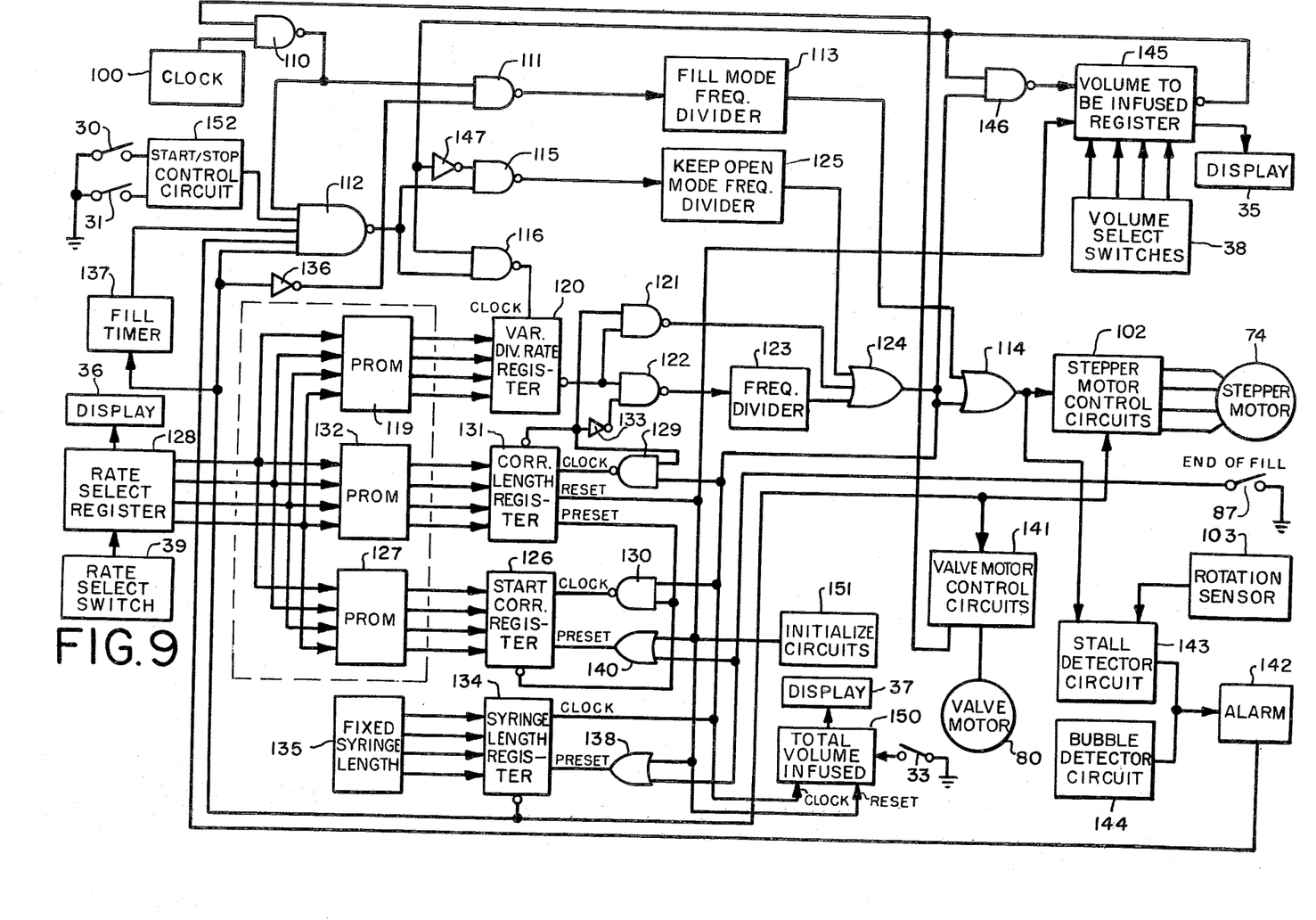
FIG. 9 is a simplified functional block diagram of the pump control system.

Referring to FIG. 9, the constant-frequency output pulses developed by clock 100 are applied through a NAND gate 110 to a two input NAND gate 111 and a five input NAND gate 112. When NAND gate 111 is enabled, as during each fill stroke of plunger 55, the pulses are applied to a fill mode frequency divider 113 which divides the clock frequency pulses to obtain a frequency suitable for causing the stepper motor to drive the plunger to an open position during the fill strokes. In practice, the fill may be accomplished at a rate of 2000 milliliter per hour, or at a pulse rate of 55.5 hertz, so that the plunger is driven to its full open position in slightly less then eight seconds. The fill-frequency motor control pulses thus derived from divider circuit 113 are applied to stepper motor control circuits 102 through an OR gate 114. Within motor control circuits 102 the pulses cause the generation of multiphase control signals for application to stepper motor 74 in a manner well known to the art.

During each pump stroke the constant-frequency pulses from clock 100 are applied through NAND gate 112 to respective inputs of NAND gates 115 and 116. During pump operation in other than a keep open mode NAND gate 116 is enabled, and the pulses thus applied to the gate are applied to the clock input of a variable rate divider register 120. The division rate of register 120 is dependent on an applied BCD signal RATE derived from an associated PROM 119, and may in practice be such that the output of register 120 is at the correction rate NpR, or four times the operator-selected rate in the present embodiment. The output of register 120 is applied to respective inputs of NAND gates 121 and 122. During periods $X_1$-$X_2$, when the pump stroke is being accomplished at a normal rate R, NAND gate 122 is enabled and the high-rate pulses from register 120 are applied to a frequency divider circuit 123. This circuit divides the pulses by an appropriate factor Np, in this case four, to obtain pulses at the desired flow rate R. These pulses are applied to one input of an OR gate 124, and through the remaining input of OR gate 114 to stepper motor control circuit 102. During those portions of the pump stroke $X_0$-$X_1$ and $X_2$-$X_3$ wherein the plunger operates at the high compensating rate, e.g. four times desired flow rate, NAND gate 121 is enabled and the high-rate pulses are applied directly to another input of OR gate 124, and through OR gate 114 to motor control circuits 102.

After a desired quantity of fluid has been pumped, the control system may be conditioned to operate the pump in a so-called "keep open" mode, wherein a minimum low pump rate is maintained to avoid clotting and to render the flow system available for immediate use. To this end, upon completion of an operator-designated fluid volume NAND gate 115 is enabled and the clock-rate pulses from clock 100 are applied to a "keep open" mode frequency divider circuit 125 which introduces a suitable division factor to provide a very low flow rate, typically in the order of 5 milliliters per hour. These low-rate pulses are applied through OR gates 124 and 114 to the stepper motor control circuit 102.

If one complete operating cycle of the syringe plunger is considered as starting at $X_1$ and ending at $X_5$ (FIG. 8), then the first correction period appearing in that cycle, $X_2$-$X_3$, will begin after $X_2$-$X_1$ steps have been taken by stepper motor 74. This number, hereinafter referred to as CORECT, is loaded into a register 126 upon application of a signal to the preset input of the register. The number CORECT is a variable dependent on the rate R selected by the operator, and the preselected correction rate NpR, and is derived in the illustrated embodiment by means of a PROM 127 addressed by a BCD signal derived from the operator-set rate select switches 39 and a rate select register 128. Once loaded, register 126 is decremented by stepping pulses at the output of OR gate 124, which are applied to the clock input of the register through a NAND gate 130. When register 126 is decremented to zero, indicating that the desired number of steps CORECT have been accomplished by the stepper motor, a logic low output is generated which inhibits NAND gate 130 to prevent the application of further stepping pulses to the register.

The output off register 126 is also applied to the preset input of a correction length register 131. This causes register 131 to assume the counting state existing at the output of a PROM 132, which comprises a variable TALLY representing the length of the total correction to be applied in each pump cycle. This length two which is illustrated by the segment $X_2$ to $X_3$ and $X_4$ to $X_5$ in FIG. 8, is different for each rate selected by the operator, since the fill stroke is constant and represents a variable percentage of the total pump cycle depending on the selected rate. In the illustrated embodiment, TALLY is determined by PROM 132 according to the BCD signal applied to the PROM by rate select switches 128.

Once TALLY has been loaded into register 131, the output of the register is logic high. This causes NAND gate 121 to be enabled and NAND gate 122 to be inhibited through inverter 133. Consequently, frequency divider 123 is bypassed and pulses at the higher-frequency correction rate NpR are applied to stepper motor control circuits 102 to cause the syringe plunger to be driven forward at a high rate.

The motor control pulses applied to stepper motor control circuits 102 are also applied to the clock input of a syringe length register 134, causing that register to decrement from a previously loaded BCD input from a fixed syringe length initiating source 135 indicative of available syringe length. As a result, when the syringe reaches the end of the available pump stroke, corresponding, for example, to 350 stepping pulses, which is the number preset into counter 134 by source 135, a logic low output is produced by the register. This output is applied to one input of NAND gate 112, causing that gate to be inhibited and thereby preventing the further application of stepping pulses to stepper motor control circuits 102 through register 120. The output of register 134 is also applied through an inverter 136 to NAND gate 11, enabling that device and allowing pulses to be applied through fill frequency divider 113 and OR gate 114 to the stepper motor control circuits 102. Since no pulses are present at the output of OR gate 124, registers 126, 131 and 134 do not receive stepping pulses during the fill stroke.

The output of register 134 is also applied to the stepper motor control circuits 102 to condition those circuits to operate stepper motor 72 in a reverse direction. At the same time, the output of register 134 is applied to a fill timer circuit 137 which provides an inhibiting signal to NAND gate 112 for a predetermined period of time slightly greater than that required to cause the stepper motor to complete the fill stroke. At the completion of the predetermined time period, the output of timer circuit 137 is again logic high so as to not inhibit NAND gate 112.

Prior to timer circuit 136 timing out, plunger 55 reaches the end of its fill stroke and actuates limit switch 87. This switch, which may be a conventional mechanical type switch, or a magnetic proximity-type switch, causes a logic low to be applied through an OR gate 138 to the preset input of register 134. This causes the fixed length constant in source 135 to be preset into the register, and the register to assume a logic high at its output. Consequently, NAND gate 112 is enabled and NAND gate 111 is inhibited. When timer circuit 137 subsequently times out, NAND gate 112 is enabled and the pump stroke begins. At the same time the logic high output of register 134 conditions stepper motor control circuits 102 to again drive stepper motor 74 in a forward or pump stroke direction.

The actuation of end of fill switch 87 also causes a logic low signal to be applied through an OR gate 140 to the present input of register 126. As a result, the output CORECT of PROM 127 is again loaded into register 126 so that a correction will again be initiated when the plunger reaches position $X_2$ in its next operating cycle.

The plunger operates at the correction rate during the first portion $X_4$–$X_5$ of the next pump stroke since correction length register 131 has not yet been decremented to zero. The stepping pulses now applied to stepper motor control circuits 102 through OR gate 124 are applied through a NAND gate 129 to the clock input of register 131. When the required number of stepping pulses have been applied, indicating completion of the correction sequence, and arrival of the plunger at $X_5$, a logic low output is produced by the register. This inhibits NAND gate 121 and enables NAND gate 122 through inverter 133. As a result, normal-rate pulses are now applied to stepper motor control circuits 102 and the stepper motor operates at the user-selected rate R, as determined by rate select switches 39 and the output RATE of PROM 119.

To provide for operation of the cassette valve 47 by valve actuator motor 80 the output of register 134 is applied to valve motor control circuits 141, which cause the valve motor to position the cassette valve as appropriate to the operating state of the plunger. Should the valve fail to move for some reason, such as binding of the valve member in the cassette housing, valve control circuits 141 include position detection circuitry which responds to the failure of the valve to produce a logic low output signal. This signal is applied to an alarm circuit 142 and to NAND gate 110 to inhibit that gate and prevent the application of pulses from clock 100 to the control circuits. As a result, alarm 142 is sounded and operation of the pump is terminated.

As a protection against stalling of stepper motor 74, the control system includes a stall detector circuit 143 which continuously compares the motor control pulses applied to the motor control circuits 102 with pulses generated by a rotation sensor 103 responsive to rotation of the stepper motor drive shaft. When a discrepancy is detected by this circuit, which may be conventional in design and construction, an output signal is produced which interrupts the output of clock 100 and sounds alarm 142. Protection against the infusion of bubbles is provided by a bubble dection circuit 144 which responds to bubble detector station 23 detecting an absence of fluid in tubing segment 14 to produce an output signal. This causes alarm 142 to sound and NAND gate 110 to be inhibited to terminate operation of the pump.

A count representing the volume to be infused is developed in a register 145. This register is decremented by motor control pulses from OR gate 124 during each pump stroke through a NAND gate 146. Upon being decremented to zero, register 145 produces a logic low output which inhibits gate 146 to prevent the application of further stepping pulses to the register. The output of register 145 is also applied to NAND gate 116 to inhibit that device, and through an inverter 147 to NAND gate 115 to enable that device. As a result, clock pulses from NAND gate 112 are applied through NAND gate 115 to the keep open mode frequency divider 125, which produces motor control pulses at a low keep open rate to maintain fluid flow through the system.

The total volume infused by the pump apparatus is stored in a total volume infused register 150. Motor control pulses from OR gate 124 are applied to the clock input of this register, and the counting state is displayed in the associated total volume display 36.

Upon initial power up of the pump, a reset circuit 151 is caused to produce a logic low output which is applied through OR gate 138 to the preset input of register 134, through OR gate 140 to the preset input of register 126, to the reset inputs of registers 131 and 150, and to the preset input of register 145. As a result, these registers are conditioned to begin a new operating cycle.

While discrete components have been utilized in the control system shown in FIG. 9, it will be appreciated that portions of this system may be incorporated into a lesser number of stages through microcomputer technology. For example, the functions of PROMS 121, 127 and 132 may be accomplished by an appropriately programmed microprocessor wherein the variables RATE, CORECT and TALLY are calculated by appropriate analgorhythms from instructions within the microprocessor.

The pump may be conveniently started and stopped by the operator by means of a control circuit 152 which is conditioned to run and stop modes by push button switches 30 and 31 on front panel 22. The output of control circuit 152 is applied to an input of NAND gate 110 and is logic low to disable that gate when the control circuit is in the standby mode.

In the above system, for example, for a designated rate R and a clock frequency $f_c$, and a syringe providing a 0.01 millileter fluid delivery with each incremental movement of the stepper motor, the variable RATE applied to register 120 can be calculated:

$$\text{RATE} = \frac{F_c}{N_p \times R}$$

If, for example, $f_c = 27600$ HZ and R = 100 ml/hr and $N_p = 4$, then $$RATE = 2484$$

To enable each pump stroke to be compensated for loss of pumping effect during the preceeding fill stroke, the duration of each fill period is fixed by fill timer 137, regardless of the actual time required to accomplish the fill stroke, which may vary with fluid viscosity and other factors. In the present embodiment, for example, the fill period is 8.0 seconds, although only 7.6 seconds is required to actually complete the fill stroke. Once the fill stroke has been completed, the plunger remains stationary at the filled position until the pump stroke begins.

Knowing the fixed fill period $T_F$, the desired pump rate R, and the selected compensation rate NpR, the number of stepping pulses to be counted during the compensation mode, TALLY, can be determined.

$$\text{TALLY} = T_F \times R \times \frac{4}{3}$$

In the case of Np=4, as in the illustrated embodiment, a 4/3 factor is necessary because for every four compensation stepping pulses one actual stepping pulse occurs.

For optimum averaging of flow over the fill-pump cycles, approximately half of the higher rate compensation of the pump stroke is accomplished before fill, and the remaining half is accomplished after refill. To this end, the variable CORECT, which determines the point $X_2$ in the stroke where the first band of compensation begins, is calculated $$\text{CORECT} = 350 \text{ steps} - \frac{\text{TALLY}}{2}$$

With the variables RATE, TALLY and CORECT thus determined, the control system of FIG. 9 operates as previously described.

For a typical operator-selected infusion rate of 100 ml. per hour and a pump increment of 0.01 ml./step, a stepping pulse frequency of 2.75 hertz is required. This requires that the variable RATE be 2484. With a fill period of 8.0 seconds, TALLY is 29 and CORECT is 350−(14)=336.

It will be appreciated that with a compensation rate other than 4x, TALLY and CORECT will change. Also, with some sacrifice in the flow regularity of the average flow rate, the two compensation bands can be formed unequally, with a greater portion of the pump stroke being compensated on either the front or rear of the fill stroke.

While a particular embodiment of the invention has been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

We claim:

1. Metering apparatus for use in conjunction with a fluid flow system for infusing fluids at an operator-selected rate into the human body, comprising:

metering means including valving means, and a syringe pump having a pump housing and a plunger, said plunger being arranged for reciprocative movement within said housing to provide alternate fill and pump strokes, for establishing in cooperation with said valving means fluid flow through the system;

actuator means for operatively engaging and reciprocatively driving said plunger to alternately provide fill strokes of relatively short duration, and pump strokes of relatively longer duration at the operator-selected flow rate, the average flow through the flow system as a result thereof being less than the operator-selected rate as a result of said intervening fill strokes; and flow compensation means for increasing the rate of each of said pump strokes from the operator-selected rate to a relatively higher compensation rate for a first predetermined compensation period immediately following each preceding fill stroke, and for a second predetermined compensation period immediately preceding each succeeding fill stroke, the intervening portion of each pump stroke being at the operator-selected rate, said compensation periods each comprising a substantial portion of a total compensation period during the pump stroke which compensates for the non-occurrence of pumping action during a fill stroke, whereby the resulting average flow rate through the flow system comprises the operator-selected rate.

2. Metering apparatus as defined in claim 1 wherein said first and second predetermined compensation periods are substantially equal.

3. Metering apparatus as defined in claim 1 wherein said syringe pump is contained within a disposable cassette, the actuator means include actuator station, and said cassette is removably received by said actuator station.

4. Metering apparatus as defined in claim 3 wherein said actuator station includes a reciprocatively driven projecting actuator member, and said plunger is detachably coupled to said member.

5. Metering apparatus as defined in claim 1 wherein said valving means of the flow system comprises a flow control valve, and said actuator means include valve control means for positioning said valve in a first position during said fill stroke, and in a second position during said pump stroke.

6. Metering apparatus as defined in claim 1 wherein said compensation rate is approximately four times the uncompensated pump stroke rate.

7. Metering apparatus as defined in claim 1 wherein said first and second predetermined compensation periods vary as a percentage of the pump stroke according to the operator-selected flow rate.

8. Metering apparatus as defined in claim 1 wherein said actuator means comprise a stepper motor responsive to applied stepping pulses for driving said syringe, and wherein said actuator means provide stepping pulses to said motor to drive said plunger in said fill and pump strokes.

9. Metering apparatus as defined in claim 8 wherein said flow compensation means include first register means for counting the stepping pulses applied to said motor during said pump stroke, said compensation periods being initiated following the counting of predetermined numbers of said applied stepping pulses.

10. Metering apparatus as defined in claim 9 wherein said flow compensation means include second register means for determining the duration of said compensation periods, said second register means being responsive to the counting of a predetermined number of said applied stepping pulses for terminating said compensation periods.

11. Metering apparatus as defined in claim 10 including computation means responsive to the operator selected rate for establishing said first and second predetermined numbers of stepping pulses required by said first and second register means.

12. Metering apparatus as defined in claim 11 wherein said computation means comprise a microprocessor.

13. The method of infusing fluids through an infusion system at a designated operator-selected rate by means of a syringe-type pump in the system into the human body, comprising the steps of:

driving the plunger of the syringe-type pump in alternate fill and pump strokes, and valving the flow system to direct the consequent repetitive filling and emptying of the syringe pump chamber to cause fluid flow through the system, the nominal speed of each pump stroke being at a rate corresponding to the operator designated flow rate; and compensating the flow rate in the system for intervening fill strokes by increasing the speed of the plunger for a first portion of each pump stroke immediately preceding each fill stroke, and for a second portion of each pump stroke immediately following each fill stroke, while maintaining the speed of the plunger at the operator-selected rate in the intervening portion of each pump stroke, the first and second compensating portions each comprising a substantial portion of a total compensation period during the pump stroke which compensates for the non-occurrence of pumping action during a fill stroke, whereby the average flow rate through the system substantially corresponds to the operator designated rate.

14. The method of infusing fluids as defined in claim 13 wherein the first and second compensating portions of each pump stroke are substantially equal.

15. Metering apparatus for use in conjunction with a fluid flow system for infusing fluids at an operator-selected rate into the human body, comprising:

metering means including valving means, and a syringe-type pump in the flow system having a pump housing and a plunger mounted for reciprocative movement within the housing to provide in cooperation with the valve means alternate fill and pump strokes for establishing fluid flow through the system;

actuator means including a motor responsive to applied stepping pulses for operatively engaging and reciprocatively driving said plunger;

motor drive means for providing stepping pulses to said motor, said stepping pulses occurring at a first relatively high predetermined frequency to advance the plunger at a relatively rapid rate during each fill stroke, and at a second relatively low predetermined frequency to advance the plunger at the operator-selected flow rate during each pump stroke, the average flow through the flow system as a result thereof being less than the operator-selected rate as a result of the intervening fill strokes; and flow compensation means for increasing the frequency of said stepping pulses from said second predetermined frequency to a higher compensating frequency for a first predetermined compensation period immediately following each preceding fill stroke, and for a second predetermined compensation period immediately preceding each succeeding fill stroke, the intervening portion of each pump stroke being at said operator-selected rate, said compensation periods each comprising a substantial portion of a total compensation period during the pump stroke which compensates for the nonoccurrence of pumping action during a fill stroke, whereby the resulting average flow rate through the infusion system comprises the operator-selected rate.

16. Metering apparatus as defined in claim 7 wherein said first and second compensation periods are substantially equal.

17. Metering apparatus as defined in claim 15 wherein said compensation means include first register means for counting the stepping pulses applied to said motor during each pump stroke, said compensation periods being initiated following the counting of a predetermined numbers of said applied stepping pulses.

18. Metering apparatus as defined in claim 17 wherein said flow compensation means include second register means for determining the duration of said compensation periods, said second register means being responsive to the counting of a predetermined number of said applied stepping pulses for terminating said compensation periods.

19. Metering apparatus as defined in claim 18 including computation means responsive to the operator designated rate for establishing said first and second predetermined numbers of counted stepping pulses required by said first and second register means.

20. Metering apparatus for use in conjunction with a disposable single-use fluid flow system of the type having valving means, and a syringe-type cassette pump having a pump housing and a plunger mounted for reciprocative movement within the pump housing to provide alternate fill and pump strokes for establishing in cooperation with the valving means fluid flow through the system for infusing fluids at an operator-selected rate into the human body, comprising:

actuator station means for receiving and fixedly positioning the cassette pump;

actuator means for operatively engaging and reciprocatively driving the plunger while positioned in said actuator station to provide fill strokes of relatively short duration, and pump strokes of relatively longer duration at the operator-selected flow rate, the average flow through the flow system as a result of the intervening fill strokes being less than the operator-selected rate; and flow compensation means for increasing the rate of each of said pump strokes from the operator-selected rate to a relatively higher compensation rate for a first predetermined compensation period immediately following each preceding fill stroke, and for a second predetermined compensation period immediately preceding each succeeding fill stroke, the intervening portion of each pump stroke being at the operator-selected rate, said compensation periods each comprising a substantial portion of a total compensation period during the pump strokes which compensates for the non-occurrence of pumping action during a fill stroke, whereby the resulting average flow rate through the flow system comprises the operator-selected rate.

21. Metering apparatus as defined in claim 20 wherein said first and second compensation periods are substantially equal.

22. Metering apparatus as defined in claim 20 wherein said actuator means include a reciprocatively driven actuator member projecting from said housing, and the plunger is detachably coupled to said actuator member.

23. Metering apparatus as defined in claim 20 wherein the valving means of the flow system comprise a flow control valve, and said actuator means include valve control means for positioning the valve in a first position during the fill stroke, and in a second position during the pump stroke.

24. Metering apparatus as defined in claim 20 wherein said actuator means comprise a stepper motor responsive to applied stepping pulses for driving said syringe, and wherein said actuator means provide stepping pulses to said motor to drive said plunger in said fill and pump strokes.

25. Metering apparatus as defined in claim 24 wherein said flow compensation means include first register means for counting the stepping pulses applied to said motor during said pump stroke, said compensation periods being initiated following the counting of predetermined numbers of said applied stepping pulses.

26. Metering apparatus as defined in claim 25 wherein said flow compensation means include second register means for determining the duration of said compensation periods, said second register means being responsive to the counting of a predetermined number of said applied stepping pulses for terminating said compensation periods.

27. Metering apparatus as defined in claim 26 including computation means responsive to the operator selected rate for establishing said first and second predetermined numbers of stepping pulses required by said first and second register means.

28. Metering apparatus as defined in claim 27 wherein said computation means comprise a microprocessor.

29. Metering apparatus as defined in claim 20 wherein said compensation rate is approximately four times the uncompensated pump stroke rate.

30. Metering apparatus for use in conjunction with a disposable single-use fluid flow system of the type including valving means, and a syringe-type cassette pump having a pump housing and a plunger mounted for reciprocative movement within the pump housing to provide alternate fill and pump strokes for establishing in cooperation with the valving means fluid flow through the system for infusing fluids at an operator-selected rate into the human body, comprising:

actuator station means for receiving and fixedly positioning the cassette pump;

actuator means including a motor responsive to applied stepping pulses for operatively engaging and reciprocatively driving the plunger while positioned in said actuator station;

motor drive means for providing stepping pulses to said motor, said stepping pulses occurring at a first relatively high predetermined frequency to advance the plunger at a relatively rapid rate during each fill stroke, and at a second relatively low predetermined frequency to advance the plunger at the operator-selected flow rate during each pump stroke, the average flow through the flow system as a result thereof being less than the operator-selected rate as a result of the intervening fill strokes; and flow compensation means for increasing the frequency of said stepping pulses from said second predetermined frequency to a higher compensating frequency for a first predetermined compensation period immediately following each preceding fill stroke, and for a second predetermined compensation period immediately preceding each succeeding fill stroke, the intervening portion of each pump stroke being at said operator-selected rate, said compensation periods each comprising a substantial portion of a total compensation period during the pump stroke which compensates for the nonoccurrence of pumping action during a fill stroke, whereby the resulting average flow rate through the infusion system comprises the operator-selected rate.

31. Metering apparatus as defined in claim 30 wherein said first and second compensation periods are substantially equal.

32. Metering apparatus as defined in claim 31 wherein said compensation means include first register means for counting the stepping pulses applied to said motor during each pump stroke, said compensation periods being initiated following the counting of predetermined numbers of said applied stepping pulses.

33. Metering apparatus as defined in claim 32 wherein said flow compensation means include second register means for determining the duration of said compensation periods, said second register means being responsive to the counting of a predetermined number of said applied stepping pulses for terminating said compensation periods.

34. Metering apparatus as defined in claim 33 including computation means responsive to the operator designated rate for establishing said first and second predetermined numbers of counter stepping pulses required by said first and second register means.

* * * * *